US00PP31516P2

(12) United States Plant Patent
Ulate

(10) Patent No.: US PP31,516 P2
(45) Date of Patent: Mar. 3, 2020

(54) ***DRACAENA* PLANT NAMED 'KRISTI'**

(50) Latin Name: *Dracaena deremensis*
Varietal Denomination: KRISTI

(71) Applicants: FLORICA FARMS, INC., Eustis, FL (US); PRIMAFLORA INTERNATIONAL LP, Fallbrook, CA (US)

(72) Inventor: William Vasquez Ulate, Alajuela (CR)

(73) Assignees: FLORICA FARMS, INC., Eustis, FL (US); PRIMAFLORA INTERNATIONAL LP, Fallbrook, CA (US)

( * ) Notice: Subject to any disclaimer, the term of this patent is extended or adjusted under 35 U.S.C. 154(b) by 0 days.

(21) Appl. No.: 15/999,877

(22) Filed: Sep. 7, 2018

(51) Int. Cl.
*A01H 5/02* (2018.01)
*A01H 6/12* (2018.01)

(52) U.S. Cl.
USPC ..... Plt./383
CPC ..... *A01H 6/12* (2018.05)

(58) Field of Classification Search
USPC ..... Plt./383
See application file for complete search history.

*Primary Examiner* — Anne Marie Grunberg
(74) *Attorney, Agent, or Firm* — Foley & Lardner LLP

(57) ABSTRACT

The new variety 'KRISTI' is a new and distinct cultivar of *Dracaena deremensis* plant. It can reach 1.5 m in length, with an average of approximately 18-20 leaves per plant. The arrangement of the leaves is in the form of a rosette. Shows colors and variegated bands very different from its parent variety (*Dracaena deremensis* plant 'Lemon Lime', unpatented).

4 Drawing Sheets

Latin name of the genus and species of the claimed plant: *Dracaena deremensis.*

Variety denomination: KRISTI.

BACKGROUND OF THE INVENTION

The present invention relates to a new and distinct cultivar of *Dracaena* plant, botanically known as *Dracaena deremensis*, of the family of Asparagaceae, hereinafter referred to by the cultivar name 'KRISTI'.

*Dracaena* is a monocotyledonous and tropical foliage plant which can produce as a single or multi-stemmed plat, use as a house plant or outdoors in shade in zones 9 or 10 only.

The new *Dracaena* 'KRISTI' originated as a naturally-occurring whole plant mutation of the *Dracaena deremensis* var. 'Lemon Lime'. The new *Dracaena* 'KRISTI' was discovered and selected by the inventor, William Vásquez Ulate in 2013, as a single sprouting within a controlled environment, in Candelaria, Palmares, Alajuela province, Costa Rica.

Asexual reproduction of the new *Dracaena* 'KRISTI' by vegetative cuttings was first performed in 2013 in Candelaria, Palmares, Alajuela province, and demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'KRISTI', which in combination distinguish this *Dracaena* as a new and distinct cultivar:

1. Strong yellowish green colored foliage, and green colored stripes in the center of the leaf.
2. Wide and lanceolate leaves, 45-50 cm long and supported in a rosette.
3. 60 cm-200 cm plant height.
4. Erect Plant habit Plants of the new *Dracaena* 'KRISTI' differ from plants of the parental cultivar, *Dracaena deremensis* 'Lemon Lime' (unpatented) in the characteristics described in Table 1.

TABLE 1

Comparison between 'KRISTI' and 'Lemon Lime'

| Characteristic | New Cultivar 'KRISTI' | Parent *Dracaena deremensis* 'Lemon Lime' (unpatented) |
|---|---|---|
| Plant Vigor | Similar vigorous | similar vigorous |
| Color | Strong yellowish colored foliage, with central stripes dark green. | tri-colored foliage, bright lime green with thin central stripes of cream and dark green. |
| Shape | lanceolate leaves on a rosette | lanceolate and leaves on a rosette |
| Texture of leaves | Smooth and waxy | Smooth and waxy |

Of the many commercial cultivars known to the present inventor, the most similar in comparison to the new *Dracaena deremensis* 'KRISTI' is the parental cultivar 'Lemon Lime'. As an additional commercial comparison, plants of the new *Dracaena* 'KRISTI' differ from plants of the comparable variety, *Dracaena deremensis* 'Eve' (U.S. Plant Pat. No. 27,073) in the characteristics described in Table 2.

TABLE 2

Commercial Comparison between 'KRISTI' and 'Eve'

| Characteristic | New Cultivar 'KRISTI' | Comparable Variety *Dracaena deremensis* 'Eve' (U.S. Plant Pat. No. 27,073) |
|---|---|---|
| Color | Strong yellowish colored foliage, with central stripes dark green. | Strong yellowish and brilliant yellowish green foliage with brilliant yellowish green colored margins |
| Shape | lanceolate leaves on a rosette | lanceolate with curved downwards tips |
| Texture of leaves | Smooth and waxy | Smooth and waxy |

BRIEF DESCRIPTION OF THE PHOTOGRAPHS

The accompanying photographs illustrate the overall appearance of the new *Dracaena deremensis* cultivar 'KRISTI' showing the colors as true as is reasonably possible with colored reproductions of this type. Colors in the photographs may differ slightly from the color value cited in the detailed botanical descriptions which accurately describe the color of 'KRISTI'.

DETAILED BOTANICAL DESCRIPTION

Figure 1:
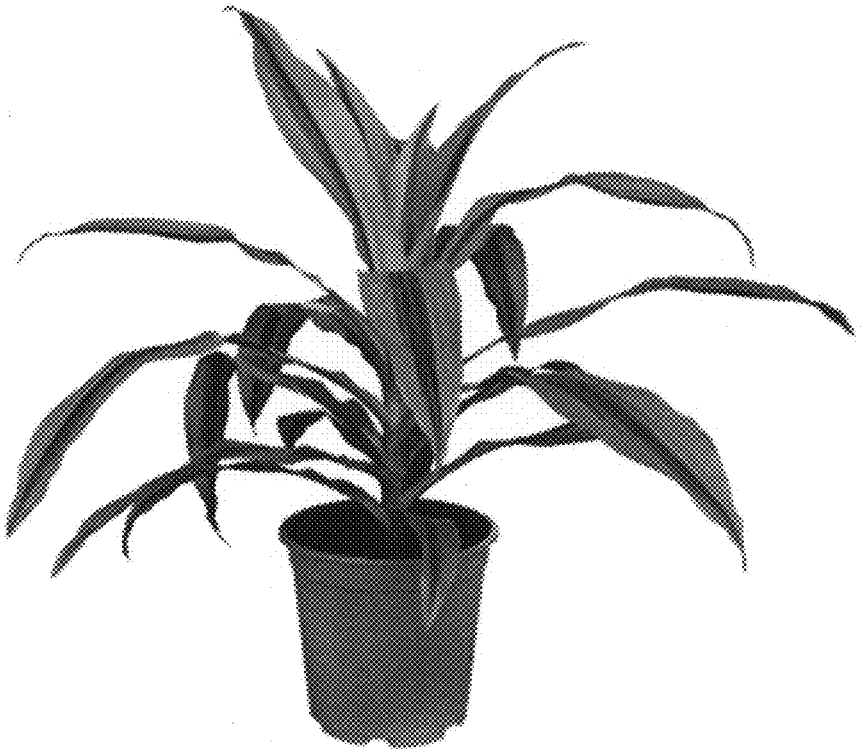
FIG. 1 shows a side view of an eight-month old plant of *Dracaena* 'KRISTI' in a 21 cm diameter pot.
Figure 2:
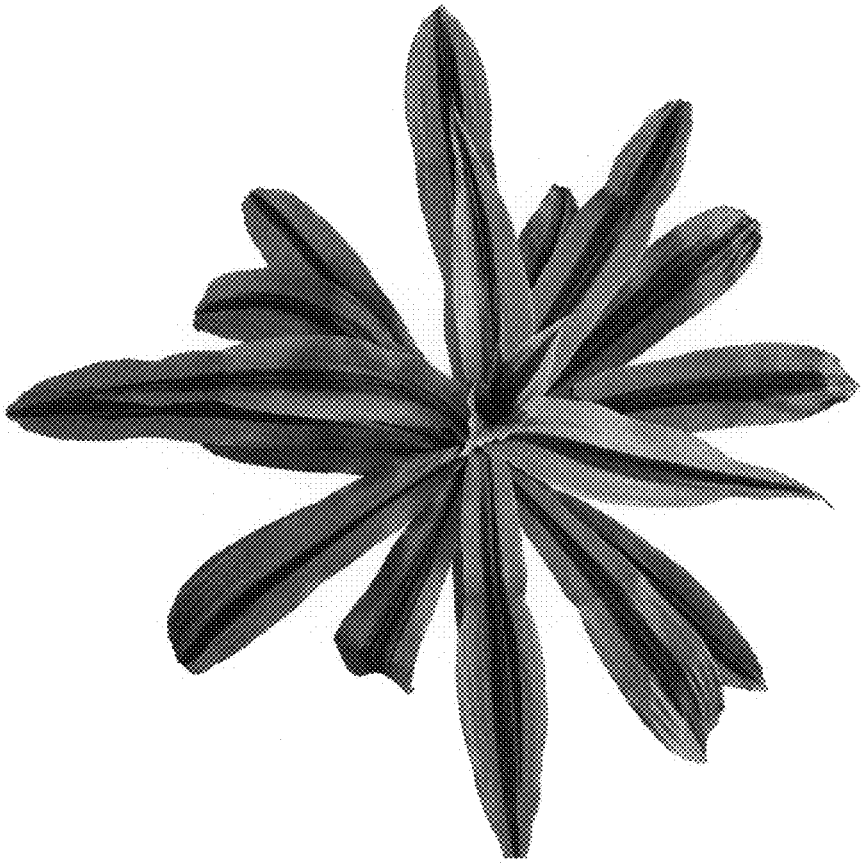
FIG. 2 shows a top view of an eight-month old plant of *Dracaena* 'KRISTI' in a 21 cm diameter pot.
Figure 3:
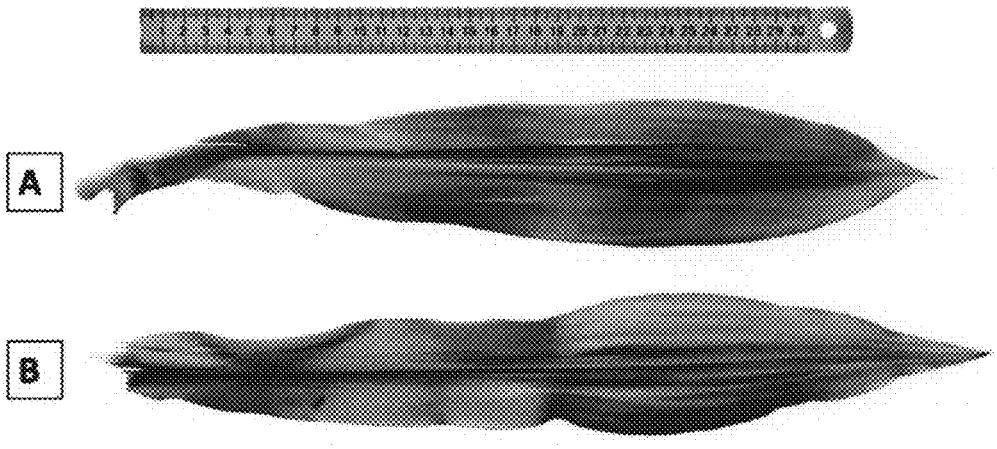
FIG. 3 shows a close-up view of the typical leaves of *Dracaena* 'KRISTI' from an eight-month old plant (upper side—A, under side—B).
Figure 4:
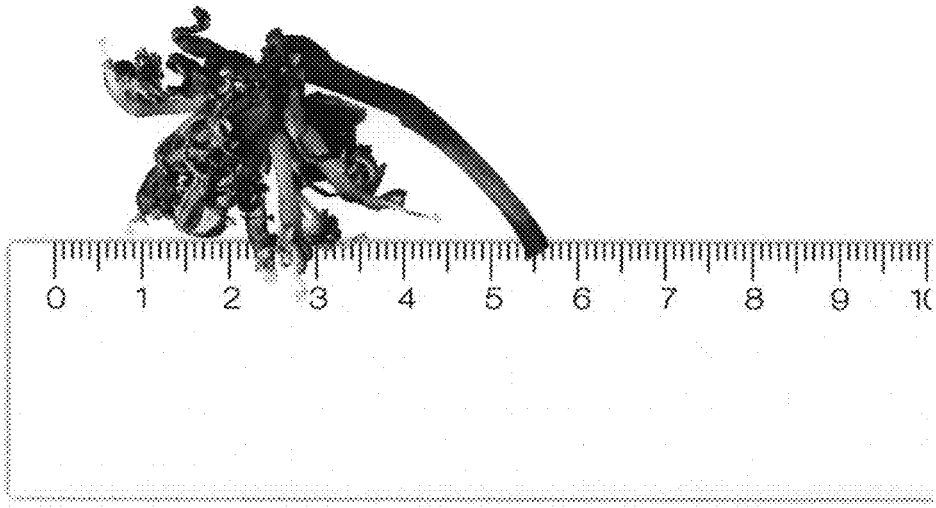
FIG. 4 shows a close up view of the inflorescence of *Dracaena* 'KRISTI'.

The new *Dracaena* 'KRISTI' has not been observed under all possible environmental conditions. The phenotype of the new cultivar may show phenotypical changes with variations in environment such as temperature, light intensity, and day length without any change in the genotype of the plant.

The aforementioned photographs, together with the following observations, measurements and values describe the new *Dracaena* cultivar 'KRISTI' as grown in open-field conditions at Candelaria, Palmares, Alajuela province, Costa Rica, which closely approximate those generally used in commercial practice. Average temperature at Candelaria is 27° C. during the day and 15° C. at night. Plants grow under natural light conditions.

Plants of the new *Dracaena* cultivar 'KRISTI' are grown under light conditions of about 80% shade from natural sunlight and about 80% relative humidity. No supplementary artificial light is necessary. Plants of the new *Dracaena* 'KRISTI' are given 1) a liquid 24-8-16 fertilizer every 15$^{th}$ days, and 2) a granular Nutricote 18-6-12 fertilizer every 6 weeks in raining season. No growth retardants are used when growing plants of the new *Dracaena* 'KRISTI'.

Color references were made according to The Royal Horticultural Society Colour Chart (R.H.S.). The photographs and descriptions were made during the dry season in Candelaria, Palmares, Alajuela province, Costa Rica when outdoor day average temperature was 26° C. The age of the plants described is 8 months old.

Classification:

*Botanical.*—*Dracaena deremensis.*

*Variety denomination.*—KRISTI.

Parentage: Naturally-occurring mutation of *Dracaena deremensis* 'Lemon Lime' (unpatented).

Optimal growth conditions:

*Light intensities.*—High adaptability to outdoor or indoor conditions.

*Temperature.*—Day: 18° C. to 28° C. Night: 14° C. to 22° C.

*Temperature tolerance.*—Tolerant to temperatures between 12° C. and 35° C.

*Fertilization.*—A liquid 24-8-16 fertilizer every 15$^{th}$ days, and a granular Nutricote 18-6-12 fertilizer every 6 weeks.

*Growth regulators.*—Not necessary.

Propagation:

*Type.*—Vegetative, by air layer or rooted cuttings.

*Rooting habit description.*—Easy to root. Roots are mostly fibrous and finely branched.

*Time to initiate roots.*—15 to 22 days at 20-25° C.

*Faster time to produce a rooted cutting.*—About 30 to 45 days at 20-25° C.

Plant:

*General appearance and form.*—

*Height.*—About 3 m when grown on the ground; About 1 m when grown in a 21 cm size container.

*Spread.*—About 1,5 m when grown on the ground; About 50 cm when grown in 21 cm size container.

*Form.*—Monocot; leaves whorled, leaf bases wrap around the stem.

*Shape.*—Column.

*Growth rate and habit.*—About 75 cm per week; upright.

*Fragrance.*—None.

*Stem-length.*—About 3 m when grown in ground; About 1.5 m when grown in 21 cm size container. Diameter: About 50-60 cm. Shape: round. Texture: rough. Color: RHS 141C. Strength: strong and durable. Internode length: About 20 mm to 40 mm.

Foliage:

*Quantity.*—About 18-20 leaves at 45 cm.

*Arrangement and attachment.*—Single, alternate; leaves whorled; leaf bases wrap around the stem.

*Leaf length.*—About 40-45 cm.

*Leaf width.*—About 6-8 cm.

*Overall shape of leaf.*—Lanceolated.

*Apex shape.*—Acute, triangular, and curved downwards.

*Base shape.*—Plane.

*Margin.*—Sharp, smooth.

*Texture.*—Upper Surface: smooth and waxy texture. Under Surface: smooth and waxy texture.

*Pubescence.*—None.

*Color of mature leaf.*—Upper Surface: RHS149A, and RHS141B central stripes. Lower Surface: RHS149A, and RHS141B central stripes.

*Color of immature leaf.*—Upper Surface: RHS149A, and RHS141B central stripes. Lower Surface: RHS149A, and RHS141B central stripes.

*Venation.*—Pattern: longitudinal/parallel to the midrib Color. Color: None. Leaf fragrance: None.

Inflorescence description:

*Arrangement and type.*—Inflorescence.

*Orientation at opening.*—Out of the spike.

*Quantity*.—Per Plant with at least one open flower: 8 inflorescence per plant. About 100 flowers opened 2 weeks after appearance of the spike.

*Inflorescence size*.—Length: About 45 cm. Diameter: About 4 cm.

*Flower size*.—Length: About 4 cm. Diameter: About 15 mm. Depth: About 1 cm.

*Fragrance*.—None.

*Bud*.—

*Rate of opening*.—About one week, according to weather.

*Shape*.—Long.

*Length*.—About 2 cm.

*Diameter*.—About 3 mm.

*Color*.—Apex: Red RHS N34A. Base: Yellowish white RHS 150D.

*Texture* (*both surfaces*).—Smooth.

Petals:

*Quantity*.—4.

*Arrangement*.—Radial.

*Color*.—RHS N34A.

Reproductive organs:

*Androecium*.—Stamen: Number: 1 per flower. Length: About 1.5 cm. Color: RHS 155D. Anther: Length: About 2 mm. Width: About 0.5 mm. Color: RHS 155D. Filament: Length: About 1.5 cm. Color: RHS 155D. Pollen: Amount: moderate. Color: RHS 155D.

*Gynoecium*.—Pistil: Number: One per flower. Length: About 1 mm. Stigma: Length: About 0.6 mm. Width: About 1.0 mm. Color: RHS 155D. Style: Length: About 2 cm. Color: RHS 155D. Ovary: Length: About 3 mm. Width: About 2.0 mm. Color: RHS 155D. Fruit: none.

Weather resistance: Drought tolerant.

Disease/pest resistance: None observed.

Disease/pest susceptibility: None observed.

I claim:

1. A new and distinct variety of *Dracaena deremensis* plant named 'KRISTI', substantially as illustrated and described herein.

* * * * *